United States Patent [19]

Frihart et al.

[11] Patent Number: 4,725,575

[45] Date of Patent: Feb. 16, 1988

[54] SILICONE RUBBER DISPENSERS OF VOLATILE ORGANIC LIQUIDS

[75] Inventors: Charles R. Frihart, Lawrenceville; George A. Locko, Trenton, both of N.J.

[73] Assignee: Union Camp Corporation, Wayne, N.J.

[21] Appl. No.: 940,018

[22] Filed: Dec. 10, 1986

[51] Int. Cl.$^4$ ................................................ A61K 7/46
[52] U.S. Cl. ........................................ 512/4; 523/102
[58] Field of Search ...................... 252/522 D; 424/76; 523/102; 524/860; 512/4

[56] References Cited

U.S. PATENT DOCUMENTS 3,966,902  6/1976  Chromecek ........................... 424/76
4,311,695  1/1982  Starch .................................... 424/76
4,582,635  4/1986  Furuuchi et al. ...................... 424/76

OTHER PUBLICATIONS

Chem. Abst.; vol. 97, #40162p (1982).

*Primary Examiner*—James H. Reamer
*Attorney, Agent, or Firm*—Edward J. Sites

[57] ABSTRACT

Silicone rubber matrices are used to contain and dispense volatile, organic liquids. The articles, as dispensors are improved by the use of silicone rubber matrices prepared by the curing of silicone fluids selected from the group consisting of polydiphenylsiloxane, polymethylphenylsiloxane, polymethyl-3,3,3-trifluoropropylsiloxane and a polydimethylsiloxane wherein 5% or more of the methyl groups of the polydimethylsiloxane are replaced by phenyl or polar aliphatic groups. Higher loadings of the organic liquid into the rubber matrix are achieved without syneresis occurring.

4 Claims, 2 Drawing Figures

SILICONE RUBBER DISPENSERS OF VOLATILE ORGANIC LIQUIDS

BACKGROUND OF THE INVENTION

1. Field of the Invention

The invention relates to silicone rubber matrices for dispensing volatile organic liquids such as fragrances by slow-release over a period of time to the atmosphere.

2. Brief Description of the Prior Art

Silicone rubber matrices for the containment and dispensing of volatile fragrances are well known in the art; see for example Japanese Patent Application No. 82-40,558. This reference describes a fragrant, rubber-like molding material, formed by dispersing a fragrance in a polydimethylsiloxane and then carrying out a cross-linking reaction with an organometal salt to obtain a silicone rubber. The articles suffer from the disadvantage that migration of the fragrance out of the silicone rubber in the form of liquid drops occurs at even moderate loadings of volatile fragrance due to incompatibility of the silicone polymer and the volatile fragrance.

The present invention represents an advance in the art in that higher loadings of volatile organic liquids for dispensing may be achieved, without syneresis, i.e.; without migration of the liquid to a surface of the silicone rubber matrix.

An additional advantage of the present invention is that transparent products having high loadings of fragrances, in particular, fragrances containing substantial amounts of polar organic compounds, can be made.

SUMMARY OF THE INVENTION

The invention comprises a device for the slow-release of a volatile, organic liquid to the atmosphere, which comprises;

a body of a silicone rubber matrix prepared by curing a silicone fluid selected from the group consisting of polydiphenylsiloxane, polymethylphenylsiloxane, polymethyl-3,3,3-trifluoropropylsiloxane and polymethylsiloxane wherein 5% or more of the methyl groups of the polydimethylsiloxane are replaced by phenyl groups or polar aliphatic functional groups;

said matrix having dispersed therein the volatile, organic liquid.

The term "volatile, organic liquid" as used herein means a liquid organic compound, which will evaporate into the atmosphere under ambient conditions of temperature and pressure.

The devices of the invention are useful for the release of a volatile to the atmosphere over prolonged periods of time and find practical application as air fresheners, deodorizers, insect repellants, pheromone dispensors and the like.

DETAILED DESCRIPTION OF THE PREFERRED EMBODIMENTS OF THE INVENTION

Figure 1:
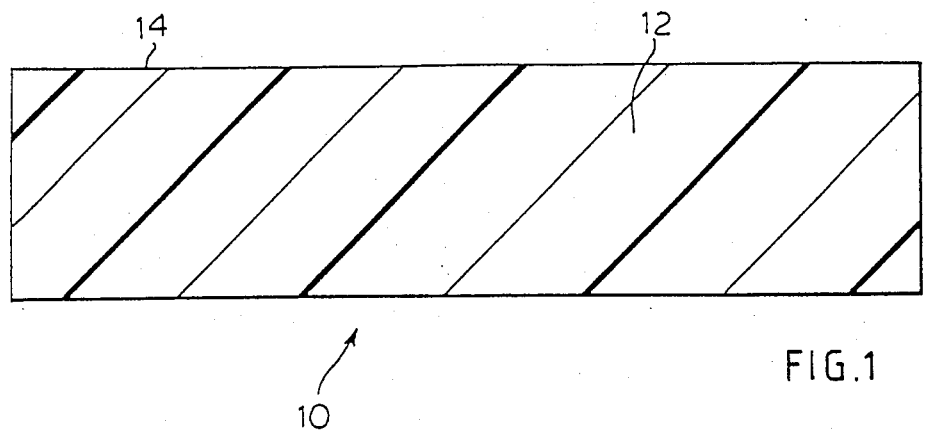
FIG. 1 is a cross-sectional side elevation of an embodiment device of the invention.

Silicone rubbers are well known compositions as are methods of their preparation. A wide variety are commercially available. In general, the silicone rubbers are prepared by curing a homogeneous mixture of silicone fluids or gums which may comprise fillers such as finely divided silica, diatomoceous earth, titanium dioxide, calcium carbonate, ferric oxide and the like; catalysts such as benzoyl peroxide, bis(2,4-dichlorobenzoyl) peroxide, t-butyl peroxybenzoate, dicumyl peroxide, organometallic salts such as dibutyltin dilaurate, and the like; pigments, solvents and like additives. The rubber compositions may be cured (vulcanized) at room temperatures (RTV) or at elevated temperatures (HTV) depending on specific catalysts and/or cross-linking agents. Representative of cross-linking agents are alkyl silicates. In the present invention, the RTV compositions are preferred since they may be cured with the volatile organic liquid in-situ, without special precautions to prevent premature volatilization and loss of the liquid due to high temperature exposure.

The volatile organic liquid may be incorporated in the silicone rubber matrix by impregnation after curing of the rubber, but preferably the liquid is admixed with the RTV rubber components prior to curing to obtain a complete and homogeneous dispersion within the cured rubber matrix. In the latter case, the volatile organic liquid is simply admixed in the curable silicone rubber composition and the composition cured. Loadings of the volatile liquid into the cured rubber may be obtained, on a weight basis, within the range of from 5 to about 40; preferably 10 to 30 and most preferably above about 20%.

The volatile organic liquid may be any volatile or volatilizable substance which it is desired to release from the polymer into the surrounding atmosphere as a gas in order to perform a useful function. The invention is particularly applicable to fragrances, including natural, essential oils and synthetic perfumes, and blends thereof. Typical perfumery materials which may form part of, or possibly the whole of, the gas for dispensing include: natural essential oils such as lemon oil, mandarin oil, clove leaf oil, petitgrain oil, cedar wood oil, patchouli oil, lavender oil, neroli oil, ylang oil, rose absolute or jasmin absolute; natural resins such as labdanum resin or olibanum resin; single perfumery chemicals which may be isolated from natural sources or manufactured synthetically, as for example alcohols such as geraniol, nerol, citronellol, linalool, tetrahydrogeraniol, betaphenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and the like.

Figure 2:
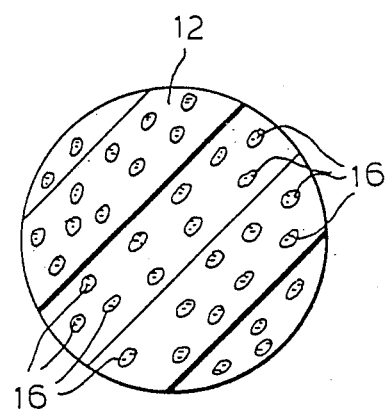
FIG. 2 is an enlarged view of a portion of the device of FIG. 1.

Referring now to the accompanying drawings, FIG. 1 is a cross-sectional side elevation of an embodiment device 10 of the invention made up of a silicone rubber matrix 12 having surfaces 14 free of migrant volatile liquid. FIG. 2 is an enlarged view of a portion of the matrix 12 having substantially dissolved therein a volatile, organic liquid plus an additional amount of the organic liquid 16 which is dispersed within the matrix 12. The liquid 16 is dispensed from the matrix 12 as a volatile over a prolonged period of time.

The following examples describe the manner and process of making and using the invention and set forth the belt mode contemplated by the inventors but are not to be construed as limiting. All parts are by weight unless otherwise indicated.

EXAMPLE 1

This is not an example of the invention, but is made for comparative purposes.

As a control, 3.0 g of silanol-terminated polydimethylsiloxane (Petrarch Systems PS-340.5; molecular weight 3200 and viscosity of 80 centipoise) and 1.77 g of polydiethoxysiloxane (Petrarch Systems PS-912) were mixed in a 2-inch diameter Teflon Petri dish. The dish was covered and the mixture was allowed to stand 24 hours. Then 1.25 g of a floral fragrance containing greater than 20% by weight of alcohols was added, followed by the addition of 0.6 g of 50% tin octoate in polydimethylsiloxane (Petrarch Systems PS-050). The two materials were vigorously mixed with a spatula. The mixture was very milky (opaque) in appearance due to the insolubility of the fragrance in the siloxane. The next day, after the mixture had cured, syneresis was observed on the top and bottom surfaces of the fragrance-containing silicone rubber disk.

EXAMPLE 2

The procedure of Example 1 was repeated, except that 3.0 g of silanol-terminated (85-88%) dimethyl-(12-15%) diphenylsiloxane copolymer (Petrarch Systems PS-084; molecular weight of 950 and viscosity of 55 centipoise) was used instead of the silanol-terminated polydimethylsiloxane. This formulation gave a cured product which was transparent, which was indicative of the good solubility of the fragrance in the rubber. A slight amount of liquid fragrance was observed on the bottom surface of the rubber disk.

EXAMPLE 3

The procedure of Example 1 was repeated, except that 3.0 g of silanol-terminated polymethyl-3,3,3-trifluoropropylsiloxane (Petrarch Systems PS-184.5; molecular weight of 550800 and viscosity of 30-50 centipoise) was used instead of the silanol-terminated polydimethylsiloxane. This formulation gave a transparent cured product, which is indicative of good solubility of the fragrance. No syneresis was observed.

What is claimed is:

1. A composition for the slow-release of a volatile, organic liquid to the atmosphere, which comprises;
   a body of a silicone rubber matrix prepared by curing a silicone fluid selected from the group consisting of polydiphenylsiloxane, polymethylphenylsiloxane, polymethyl-3,3,3-trifluoropropylsiloxane and a polydimethylsiloxane wherein 5% or more of the methyl groups of the polydimethylsiloxane are replaced by phenyl or polar aliphatic groups;
   said matrix having dispersed therein the volatile, organic liquid.

2. The composition of claim 1 wherein the silicone rubber is a room temperature vulcanized rubber.

3. The composition of claim 1 wherein the organic liquid is a fragrance.

4. The composition of claim 1 wherein the organic liquid represents, on a weight basis, from 5 to about 40 percent of the composition.

* * * * *